United States Patent [19]

Katsumata et al.

[11] Patent Number: 4,500,640
[45] Date of Patent: Feb. 19, 1985

[54] PLASMIDS

[75] Inventors: Ryoichi Katsumata, Machida; Tetsuo Oka, Yokohama; Akira Furuya, Kawasaki, all of Japan

[73] Assignee: Kyowa Hakko Kogyo Co., Ltd., Tokyo, Japan

[21] Appl. No.: 368,035

[22] Filed: Apr. 13, 1982

[51] Int. Cl.³ .................. C12N 1/20; C12N 15/00; C12N 1/00; C12R 1/13
[52] U.S. Cl. .................. 435/253; 435/172.3; 435/317; 435/840; 435/843; 935/29; 935/72
[58] Field of Search ............ 435/317, 172, 253, 172.3; 935/29, 72

[56] References Cited

U.S. PATENT DOCUMENTS

| | | | |
|---|---|---|---|
| 3,002,889 | 10/1961 | Kinoshita et al. | 435/861 |
| 3,003,925 | 10/1961 | Kinoshita et al. | 435/861 |
| 3,096,252 | 7/1963 | Motozaki et al. | 435/111 |
| 3,120,472 | 2/1964 | Dunn et al. | 435/110 |
| 3,128,237 | 4/1964 | Motozaki et al. | 435/110 |
| 3,220,929 | 11/1965 | Kinoshita et al. | 435/832 |

FOREIGN PATENT DOCUMENTS 2482622 11/1981 France .
2076853 12/1981 United Kingdom .

OTHER PUBLICATIONS

Kaneko et al., Agr. Biol. Chem., vol. 43 (4), pp. 867–868 (1979).
Chem. Abstracts 90 (1979), 90:99902p.
Chem. Abstracts 91 (1979), 91:35517c.
Chem. Abstracts 91 (1979), 91:89549k.
Humphreys et al., Biochimica et Biophysica Acta, vol. 383, pp. 457–463 (1975).

Primary Examiner—Alvin E. Tanenholtz
Attorney, Agent, or Firm—Fitzpatrick, Cella, Harper & Scinto

[57] ABSTRACT

Disclosed are novel plasmids which can replicate autonomously in microorganisms belonging to the genus Corynebacterium or Brevibacterium and which carry a gene for resistance to streptomycin and/or spectinomycin. The plasmids are useful as a cloning vector.

9 Claims, 1 Drawing Figure

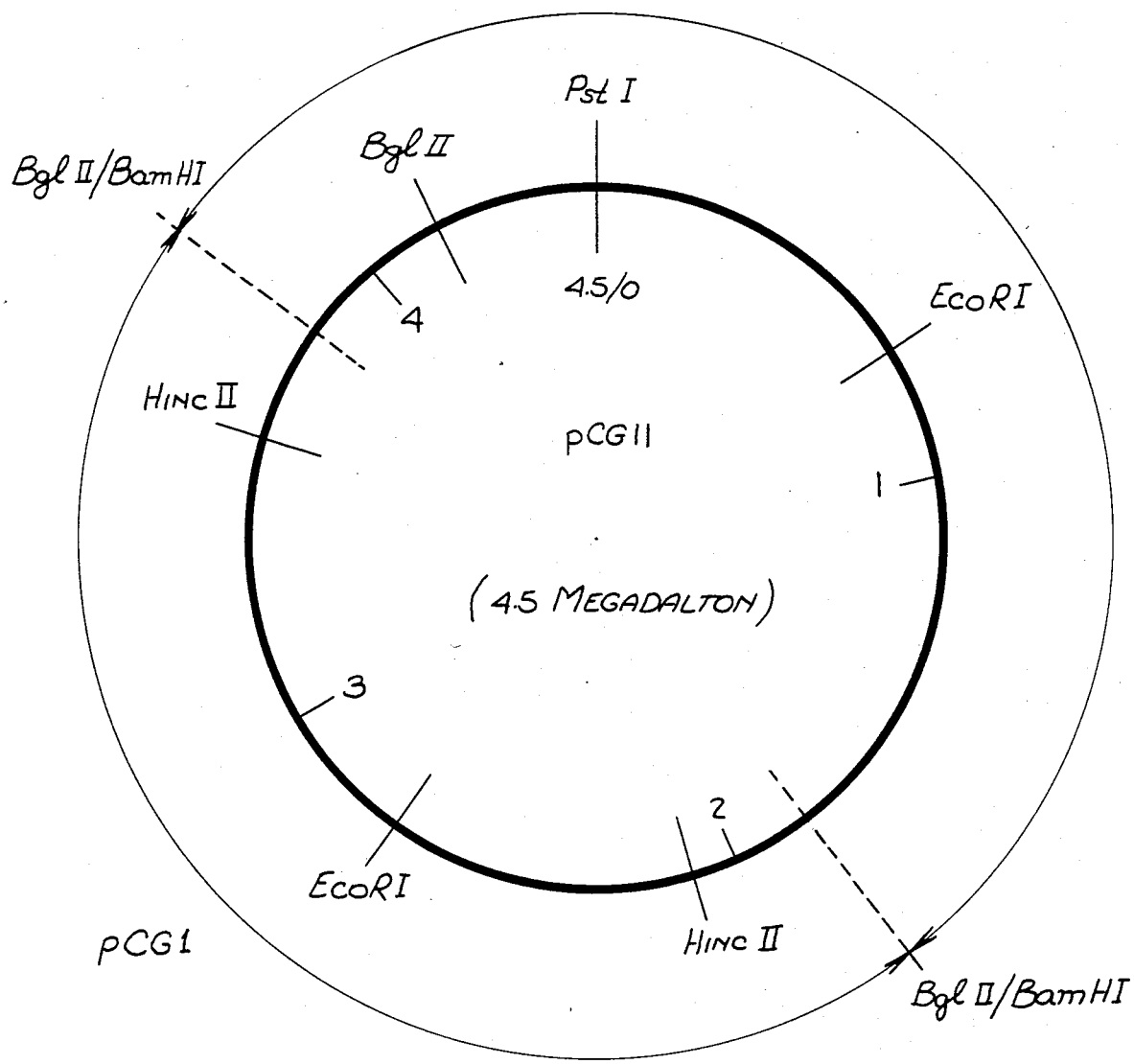

PLASMIDS

BACKGROUND OF THE INVENTION

The present invention relates to novel plasmids, and more specifically to plasmids which can replicate autonomously in a microorganism belonging to the genus Corynebacterium or Brevibacterium and carry a gene relating to resistance to streptomycin and/or spectinomycin.

The usefulness of plasmids in genetic engineering is recognized in the host-vector system of *Escherichia coli*. The role of vectors in genetic engineering is also well recognized, such as in Recombinant Molecules: Impact on Science and Society, Miles International Symposium Series No. 10, edited by R. F. Beers and E. G. Basset, Raven Press, New York.

Recombinant DNA technology has, of late, been developed on industrially useful microorganisms other than *Escherichia coli*, such as amylase-producing *Bacillus subtilis*, antibiotics-producing Actinomycetes and alcohol-producing yeasts. Since vectors are essential for recombinant DNA technology, plasmids and phages adaptable to these industrially useful microorganisms are in need. To this end, novel plasmids have been isolated from the organism, *Corynebacterium glutamicum* 225-250, which are useful as a vector in industrial microorganisms such as *Corynebacterium glutamicum* and analogous species which are used for the production of such commercial substances as glutamic acid, lysine and the like.

SUMMARY OF THE INVENTION

In accordance with the present invention novel plasmids are prepared which can replicate autonomously in a microorganism belonging to the genus Corynebacterium or Brevibacterium and which carry a gene for resistance to streptomycin and/or spectinomycin. Since the plasmid of the present invention includes a gene for resistance to streptomycin and/or spectinomycin on the DNA, it is employed for assigning the phenotype of resistance to both reagents to a host microorganism. This property permits the effective selection of a microorganism containing a recombinant plasmid carrying an objective gene. Thus, the plasmid is very useful as a cloning vector in microorganisms belonging to the genus Corynebacterium or Brevibacterium and analogous species thereof and as a reagent for the study of recombinant DNA technology.

DESCRIPTION OF THE INVENTION

According to the present invention a plasmid is obtained from the cells of a microorganism belonging to the genus Corynebacterium or Brevibacterium. An example of a particularly preferred plasmid is the plasmid named pCG 4. Plasmid pCG 4 has the following characteristics:

(1) Plasmid pCG 4 is a deoxyribonucleic acid with a molecular weight of about 19 megadaltons.
(2) Plasmid pCG 4 has the following cleavage sites for the identified restriction endonucleases.

| Enzyme* | Number of cleavage sites |
|---|---|
| Eco RI | 4 |
| Bam HI | 7 |
| Hind III | 9 |
| Pst I | 6 |
| Sal I | 6 |

*These enzymes are abbreviations of the restriction endonucleases obtained from the following microorganisms.
Eco RI: *Escherichia coli*
Bam HI: *Bacillus amyloliquefaciens*
Pst I: *Providencia stuartii*
Hind III: *Haemophilus influenzae*
Sal I: *Streptomyces albus*

The number of cleavage sites for the restriction endonucleases are determined by completely digesting plasmid pCG 4 in the presence of an excess amount of restriction endonuclease, subjecting the digest to 0.8% agarose gel electrophoresis, and thereafter counting the number of isolated fragments. The molecular weight is determined by measuring the molecular weight of each fragment in the digested plasmid pCG 4 based on the standard curve plotted with electrophoretic distances on agarose gel electrophoresis for the fragments obtained by digesting λ phage DNA of *Escherichia coli* with Hind III [J. Mol. Biol., 98, 551–564 (1975)] and in the case of plural fragments, summing up the molecular weights.

Plasmid pCG 4 is obtained from *Corynebacterium glutamicum* 225-250 which was isolated from a soil sample. Properties of the 225-250 strain are set forth below. The taxonomic studies of the 225-250 strain were carried according to the procedure in *Manual of Microbiological Methods* by the Society of American Bacteriologist Committee on Bacteriological Technique (1957).

I. Morphological characteristics:
 Usually ellipsoidal or short rods 0.7–1.0 by 1.0–3.0μ; Pleomorphic due to snapping division and branching cells; Gram positive; non-motile; non-spore-forming.

II. Culture characteristics on a nutrient medium:
 On an agar plate, a single, circular, lustrous and pale yellow colony; on a slant, a similar pale yellow opaque colony; on an agar stab, abundant growth on the surface and slight growth in deep; in a liquid medium, slight growth and slightly flocculent sediment.

III. Physiological characteristics:
 (1) Temperature: optimum temperature 25°–37° C.; growth occurs slightly at 42° C.
 (2) pH: optimum pH 7–8; growth occurs at pH 6–9
 (3) Thermal resistance: none
 (4) Relation to free oxygen: aerobic
 (5) Gelatin liquefaction: none
 (6) Assimilation of casein: negative
 (7) Indole production: none
 (8) Catalase: positive
 (9) Assimilation of starch: negative
 (10) Acid production from glucose, fructose, mannose and maltose; non-acid production from xylose, galactose, lactose and glycerol
 (11) Requirement for biotin: positive
 (12) Glutamic acid is accumulated in a large quantity in a medium wherein the amount of biotin is restricted.
 (13) Lactic acid and α-ketoglutaric acid are accumulated in a medium containing biotin in a high concentration.

These characteristics are compared with those of bacteria disclosed in J. Gen. Appl. Microbiol., 73, 279–301 (1967). Since the characteristics coincide well with those of *Corynebacterium glutamicum*, the 225-250 strain is identified as a strain of *Corynebacterium glutamicum*.

In the taxonomic characteristics, there is no difference between *Corynebacterium glutamicum* 225-250 and an ordinary strain of *Corynebacterium glutamicum*. However, the former is different from the latter in maintaining the phenotype of resistance to streptomycin and spectinomycin. A derivative strain lacking the phenotype of resistance to both streptomycin and spectinomycin is isolated by subjecting the strain to a conventional plasmid curing treatment. The absence of pCG 4 in such streptomycin and spectinomycin sensitive strains shows that the gene responsible for the resistance to streptomycin and spectinomycin is carried in pCG 4.

*Corynebacterium glutamicum* 225-250 and *Corynebacterium glutamicum* 250-1 which lacks pCG 4 have been deposited with the Fermentation Research Institute, Agency of Industrial Science and Technology, Japan under accession numbers FERM-P 5939 and 5940, respectively and the American Type Culture Collection, Rockville, Md., U.S.A., under accession numbers ATCC 31830 and 31831, respectively.

In order to obtain plasmid pCG 4 from *Corynebacterium glutamicum* 225-250, the cells have to be disrupted. Since cells of microorganisms belonging to the genus Corynebacterium or analogous species, when cultured in a conventional medium, are insensitive to a bacteriolytic enzyme such as egg white lysozyme, it is necessary to induce a sensitivity to egg white lysozyme prior to use. To render *Corynebacterium glutamicum* 225-250 sensitive to lysozyme, a known method is applicable which is used for *Streptococcus faecalis* [Can. J. Microbiol., 7, 363–373 (1961)] which is gram-positive and inherently insensitive to egg white lysozyme as is the case with *Corynebacterium glutamicum*. That is, during the log phase cultivation period, an amount of penicillin which does not inhibit or sub-inhibits the growth, usually 0.1–10 U/ml culture liquor, is added to the medium and culturing is continued for several generations. By such procedure, lysozyme-sensitive cells are obtained.

For culturing, a liquid medium and methods which are usually used for microorganisms belonging to *Corynebacterium glutamicum* and analogous species thereof are employed. The cell walls of cultured cells of *Corynebacterium glutamicum* 225-250 which are treated with penicillin as mentioned above are easily disrupted with lysozyme. Plasmid pCG 4 can be then condensed and isolated from the disrupted cells by a conventional method such as disclosed in Biochim. Biophys. Acta, 383, 457–463 (1975).

That is, sodium lauryl sulfate and NaCl are added to the disrupted cells and the mixture is subjected to centrifugation to obtain a supernatant containing plasmids. Polyethyleneglycol is then added to obtain a condensed and deposited DNA. The precipitate is redissolved and subjected to ethidiumbromide-cesium chloride density gradient centrifugation to obtain plasmid pCG 4.

Heretofore, the presence of a plasmid which is autonomously replicated and has a selectable phenotype in microorganisms belonging to the genus Corynebacterium and analogous species has not been known. Plasmid pCG 4 can replicate autonomously in microorganisms belonging to *Corynebacterium glutamicum* as well as other species of Corynebacterium and Brevibacterium and assign the phenotype derived from the gene responsible for the resistance to streptomycin and spectinomycin to the host microorganism.

A suitable transformation method of these microorganisms with plasmid pCG 4 is described in a commonly owned copending application entitled "Transformation method of a microorganism". A practical embodiment of this transformation method is also described in the following Example 2; and transformants obtained by this method are shown in Table 1.

TABLE 1

| Microorganisms | pCG 4 | Minimum Inhibitory Concentration (MIC µg/ml) | |
|---|---|---|---|
| | | Spectinomycin | Streptomycin |
| *Corynebacterium glutamicum* 225-250 | + | ≧800 | 200 |
| *Corynebacterium glutamicum* 250-1 | − | 25 | 3.2 |
| *Corynebacterium herculis* ATCC 13868 | − | 25 | 3.2 |
| *Corynebacterium herculis* ATCC 13868/pCG 4 | + | ≧800 | 200 |
| *Brevibacterium flavum* ATCC 14067 | − | 25 | 3.2 |
| *Brevibacterium flavum* ATCC 14067/pCG 4 | + | ≧800 | 200 |
| *Brevibacterium lactofermentum* ATCC 13655 | − | 25 | 1.6 |
| *Brevibacterium lactofermentum* ATCC 13655/pCG 4 | + | ≧800 | 100 | strain No./pCG 4: pCG 4 transformant

The foregoing microorganisms carrying pCG 4, i.e. *Corynebacterium herculis* ATCC 13868/pCG 4, *Brevibacterium flavum* ATCC 14067/pCG 4 and *Brevibacterium lactofermentum* ATCC 13655/pCG 4 have been deposited with the Fermentation Research Institute, Agency of Industrial Science and Technology, Japan under accession numbers FERM-P 5941, 5942 and 5943, respectively and the American Type Culture Collection, Rockville, Md., U.S.A., under accession numbers ATCC 31837, 31838 and 31839, respectively.

An examination of sensitivity to streptomycin and spectinomycin of *Corynebacterium glutamicum* 225-250 which carries pCG 4 inherently, *C. glutamicum* 250-1 which is derived from the 225-250 strain by curing plasmid pCG 4 and other microorganisms transformed with plasmid pCG 4 is also set forth in the above Table 1. The minimum inhibitory concentration data represent the concentration of the reagent whereby the growth of about $10^4$ cells inoculated on NB agar medium consisting of 20 g of powdered bouillon, 5 g of yeast extract, 18 g of agar and 1 liter of water and adjusted to pH 7.2 is completely inhibited for 2 days.

A plasmid of the present invention is useful because it can replicate autonomously in industrial important microorganisms belonging to the genus Corynebacterium or Brevibacterium which are used for the production of such useful substances as amino acids, nucleic acids and the like, it has a gene responsible for resistance to streptomycin and/or spectinomycin which enables identification of the microorganism carrying the plasmid and it has cleavage sites for various restriction endonucleases.

As will be apparent from the characteristics mentioned above, the plasmid of the present invention is qualified as a vector for cloning desired genes in a host microorganism belonging to the genus Corynebacterium or Brevibacterium by conventional recombinant DNA technology. Therefore, the present invention provides a method wherein a gene responsible for the biosynthesis or regulation of useful substances such as amino acids and obtained from these bacteria or other microorganisms may be cloned to increase the productivity of the useful substances by stimulation of the biosynthetic system on the amplification of the cloned genetic information. Furthermore, the present invention provides a method wherein a gene obtained from animals or plants may be cloned to produce useful proteins by the expression of the gene. Cloning is carried out by a method wherein recombinant DNAs with vector plasmids prepared in vitro are introduced into a host microorganism and a microorganism carrying a plasmid having the objective gene is selected. The gene responsible for the resistance to streptomycin or spectinomycin on the plasmid of the present invention facilitates the selection of the microorganism with objective genes. That is, when the objective gene to be cloned has a selectable phenotype depending on the gene, the objective cloned microorganism is recognized more definitely by simultaneous selection with the phenotype resistant to streptomycin or spectinomycin. When the gene to be cloned has not any selectable phenotype, the objective cloned microorganism is obtained effectively by selecting with the phenotype resistant to streptomycin or spectinomycin.

A plasmid derivative wherein a region of the plasmid is deleted or another DNA fragment is inserted can be obtained without losing the autonomous replication function of the plasmid and/or the function of the gene involved in the expression of resistance to streptomycin and spectinomycin.

A DNA fragment containing the gene responsible for the resistance to streptomycin or spectinomycin can be combined with other plasmids not having a selectable gene by conventional recombinant technology and such recombinant is also useful as a vector.

Therefore, it should be recognized that the present invention is not restricted to the particular plasmid pCG 4 but also includes derivative plasmids modified therefrom as well as recombinants with other plasmids.

A recombinant plasmid wherein a DNA fragment containing a gene responsible for the resistance to streptomycin and/or spectinomycin derived from pCG 4 is combined with a plasmid of a microorganism belonging to the genus Corynebacterium or Brevibacterium can be prepared using conventional in vitro recombinant DNA technology. In vitro DNA recombination is carried out fundamentally by ligating a DNA fragment containing an antibiotic resistant gene derived from pCG 4 and a plasmid fragment using a DNA ligase. Fragmentation of DNA is readily carried out using conventional restriction endonucleases. Ligation is carried out using T4 phage DNA ligase. Since the enzyme can ligate not only foreign DNA fragments having a complementary single stranded end but also those having a double stranded blunt end, when the DNAs are cleaved with the same restriction endonuclease to make cohesive ends of blunt ends, they can be ligated. When the DNAs are cleaved with different restriction endonucleases, if they have blunt ends, they can be ligated. When the DNAs are cleaved with restriction endonucleases giving different cohesive ends, they can be ligated after removing the single stranded part with an exonuclease or after making a blunt end with a DNA polymerase.

Many different recombinant molecules may result from the ligation procedure mentioned above. The objective recombinant is recovered by transforming a microorganism belonging to the genus Corynebacterium or Brevibacterium with the ligated DNA mixture, selecting a transformant with a pheno-type resistant to streptomycin or spectinomycin, culturing the transformant and isolating the objective recombinant plasmid from the culture. The preparation of one such recombinant, pCG 11, is described in Example 3 below. This pCG 11 recombinant is obtained by ligating Bgl II-cleaved pCG 1, which is isolated from *Corynebacterium glutamicum* 225-57 (ATCC 31808, FERM-P 5865) as described in Reference Example 1, with the Bam HI fragment (2.5 megadaltons) containing a gene of pCG 4 responsible for the resistance to streptomycin and/or spectinomycin. The structure of the pCG 11 recombinant is characterized by the restriction map shown in FIG. 1.

Plasmid pCG 11 can be employed as a useful vector like pCG 4 since it can autonomously replicate in *Corynebacterium glutamicum* LA 103, a derivative strain of L-22 (the approved host strain for recombinant DNA experiment), and has a gene responsible for resistance to streptomycin and/or spectinomycin useful as a selection marker. Furthermore, pCG 11 is particularly useful because it has less cleavage sites with various restriction endonucleases and it can be used for cloning a DNA fragment by in vitro DNA recombinant technology without the loss of autonomous replication ability and resistant gene.

A recombinant plasmid with a fragment of pCG 4 conferring resistance to streptomycin and/or spectinomycin can be prepared by in vitro recombinant technology using any plasmid replicable in a microorganism belonging to the genus Corynebacterium or Brevibacterium. Such recombinant plasmid has the same usefulness as pCG 4. Therefore, the useful recombinant plasmids to be prepared using the plasmid of the present invention is not restricted to pCG 11.

The usefulness of the recombinant plasmid pCG 11 is illustrated using *Corynebacterium glutamicum* LA 103 as a host microorganism which is a derivative strain of L-22, the approved host in recombinant DNA experiments. *Corynebacterium glutamicum* LA 103/pCG 11 carrying the plasmid, pCG 11, has also been deposited with the American Type Culture Collection, Rockville, Md., U.S.A. under accession number ATCC 39022.

Considering the function of pCG 4 as a vector in a microorganism of Corynebacterium or Brevibacterium, it is apparent that any recombinant plasmid, including pCG 11, which is a recombinant plasmid of pCG 4 and another plasmid autonomously replicable in a microorganism of Corynebacterium or Brevibacterium can be employed generally to microorganisms of Corynebacterium and Brevibacterium.

Certain specific embodiments of the present invention are illustrated by the following representative examples reflecting actual experimental data.

EXAMPLE 1

(1) Isolation of plasmid pCG 4 from *Corynebacterium glutamicum* 225-250:

In this step, *Corynebacterium glutamicum* 225-250 is cultured with shaking at 30° C. for 18 hours in an NB medium consisting of 20 g of powdered bouillon, 5 g of yeast extract and 1 liter of water and adjusted to pH 7.2. Then, 5 ml of culture is inoculated into 400 ml of a semisynthetic medium (SSM) consisting of 20 g of glucose, 10 g of $(NH_4)_2SO_4$, 3 g of urea, 1 g of yeast extract, 1 g of $KH_2PO_4$, 0.4 g of $MgCl_2.6H_2O$, 10 mg of $FeSO_4.7H_2O$, 0.2 mg of $MnSO_4.(4-6)H_2O$, 0.9 mg of $ZnSO_4.7H_2O$, 0.4 mg of $CuSO_4.5H_2O$, 0.90 mg of $Na_2B_4O_7.10H_2O$, 0.04 mg of $(NH_4)_6Mo_7O_{24}.4H_2O$, 30 μg of biotin, 1 mg of thiamine hydrochloride and 1 liter of water (pH adjusted to 7.2). Culturing is carried out with shaking at 30° C. The optical density (OD) at 660 nm is measured using a Tokyo Koden colorimeter and, at OD 0.2, penicillin G is added to the broth to a final concentration of 0.5 U/ml. Culturing is continued at 30° C. to OD about 0.6.

The microbial cells are then recovered from the culture broth, washed with TES buffer solution (pH 8.0) consisting of 0.03M tris(hydroxymethyl)aminomethane (Tris), 0.005M EDTA and 0.05M NaCl and suspended in a lysozyme solution (pH 8.0) consisting of 25% sucrose, 0.1M NaCl, 0.05M Tris and 0.8 mg/ml lysozyme to make up 10 ml of a suspension. The suspension is incubated at 37° C. for 4 hours. Then, 2.4 ml of 5M NaCl, 0.6 ml of 0.5M EDTA (pH 8.5) and 4.4 ml of a mixed solution of 4% sodium lauryl sulfate and 0.7M NaCl are added succesively to the reaction suspension. After the mixture is stirred slowly, it is kept on an ice water bath for 15 hours. The whole lysate is put into a centrifugation tube and centrifuged under 69,400×g at 4° C. for 60 minutes to obtain a supernatant fluid. To the supernatant is added 10% by weight of polyethyleneglycol 6,000. The mixture is stirred slowly until everything is dissolved and then kept on an ice water bath. After 16 hours, the mixture is centrifuged under 1,500×g for 10 minutes to obtain a pellet. The pellet is redissolved in 5 ml of TES buffer solution and 2.0 ml of 1.5 mg/ml ethidium bromide is added. Cesium chloride is added to the mixture to adjust the density to 1.580. The solution is centrifuged under 105,000×g at 18° C. for 48 hours. After density gradient centrifugation, a circular DNA closed with a covalent bond is detected by UV irradiation as a high density band located in the lower part of the centrifugation tube. The band is taken out from the side of the tube with an injector to obtain a fraction containing plasmid pCG 4. To remove ethidium bromide, the fraction is treated five times with an equal amount of cesium chloride saturated isopropyl alcohol solution consisting of 90% by volume of isopropyl alcohol and 10% TES buffer solution. Then, the residue is subject to dialysis with TES buffer solution.

To 1 ml of the thus obtained dialysate containing plasmid pCG 4 there is added 2 ml of ethanol. The mixture is allowed to stand at −20° C. for 12 hours and is then subjected to centrifugation at 10,000×g for 30 minutes. The deposited precipitate is dried in vacuo to obtain 20 μg of plasmid pCG 4.

(2) Cleavage sites for various restriction endonucleases and molecular weight of plasmid pCG 4

In this step, 0.5 μg of plasmid pCG 4 prepared above is dissolved in 10 μl of TES buffer solution (pH 8.0) and digested with two fold or more restriction endonucleases such as Eco RI, Bam HI, Hind III, Pst I, and Sal I, (products of Takara Shuzo Co., Ltd.) under the suitable conditions for each restriction endonuclease. The digested specimen is applied to a horizontal 0.8% agarose gel containing 0.6 μg/ml ethidium bromide and electrophoresis is carried out at a constant voltage of 7 V per 1 cm in width for 3–4 hours. The number of fragments formed is counted under ultraviolet irradiation to the gel plate. The molecular weight of each fragment is determined from the electrophoretic mobility. The molecular weight is estimated based on a standard curve plotted against electrophoretic mobility of DNA fragments of known molecular weights derived from the Hind III digestion of λ phage DNA. The results are illustrated in the following Table 2.

TABLE 2

| Enzyme | Number of cleavage sites | Molecular weight of each fragment (Megadalton) | Molecular weight of pCG 4 by summing up (Megadalton) |
| --- | --- | --- | --- |
| Eco RI | 4 | 5.87, 5.41, 4.75, 4.22 | 20.25 |
| Bam HI | 7 | 8.25, 2.57, 2.51, 1.98, 1.95, 1.43, 0.8 | 19.49 |
| Hind III | 9 | 5.15, 4.62, 3.03, 1.95, 1.33, 0.97, 0.82, 0.79, 0.37 | 19.03 |
| Pst I | 6 | 7.91, 4.75, 3.62, 1.50, 1.26, 0.79 | 19.83 |
| Sal I | 6 | 7.52, 4.74, 4.14, 1.50, 1.27, 0.47 | 19.64 |

EXAMPLE 2

Preparation of pCG 4-carrying microorganisms of *Corynebacterium herculis* ATCC 13868, *Brevibacterium flavum* ATCC 14067 and *Brevibacterium lactofermentum* ATCC 13655:

In this Example, 0.075 ml of a seed culture of each of the aforementioned strains cultured in an NB medium is inoculated in 7.5 ml of SSM medium and culturing is carried out at 30° C. The optical density at 660 nm is measured using a Tokyo Koden colorimeter and at OD 0.15, penicillin G is added to a final concentration of 0.5 U/ml. Culturing is then continued to OD about 0.5. Cells are recovered from the culture broth, washed with SSM medium and suspended in 2 ml of PFM medium containing 0.5 mg/ml lysozyme. PFM medium is a two fold diluted SSM medium containing 0.4M sucrose and 0.01M $MgCl_2.6H_2O$ and adjusted to pH 7.6. The suspension is incubated at 30° C. for 12 hours to prepare the protoplast of the cells. Then, 0.5 ml of the protoplast cells is put into a small tube and centrifuged at 2,500×g for 5 minutes. Deposited cells are suspended in 1 ml of TSMC buffer solution (pH 7.5) consisting of 10 mM $MgCl_2.6H_2O$, 30 mM $CaCl_2.2H_2O$, 500 mM sodium succinate and 50 mM tris(hydroxymethyl)aminomethane (Tris) and again subjected to centrifugation and washing. Deposited cells are suspended in 0.1 ml of TSMC buffer solution with gentle shaking. To the suspension is added 0.1 ml of a DNA solution containing 0.2 μg of DNA which is prepared by diluting a pCG 4 solution two-fold with two-fold concentrated TSMC. Then, 0.8 ml of TSMC buffer solution containing 20% polyethyleneglycol 6,000 is mixed with gentle shaking. After 3 minutes, 2 ml of RCG medium consisting of 5 g of glucose, 5 g of casein hydrolysate, 2.5 g of yeast extract, 3.5 g of $K_2HPO_4$, 1.5 g of $KH_2PO_4$, 0.41 g of $MgCl_2.6H_2O$, 10 mg of $FeSO_4.7H_2O$, 2 mg of $MnSO_4.$-(4–6)$H_2O$, 0.9 mg of $ZnSO_4.7H_2O$, 0.04 mg of $(NH_4)_6Mo_7O_{24}.4H_2O$, 30 μg of biotin, 2 mg of thiamine hydrochloride, 135 g of sodium succinate and 1 liter of water, adjusted to pH 7.2, is added and subjected to centrifugation at 2,500×g for 5 minutes. The supernatant is removed and deposited protoplasts are suspended in 1 ml of RCG medium. The suspension is diluted immediately with RCG medium and spread on an RCGP agar medium which contains 3% polyvinyl pyrrolidone (the degree of polymerization, 500) and 1.4% agar in RCG medium followed by incubation at 30° C. for 10 days.

The cells grown on the RCGP agar medium are collected with a platinum loop and suspended in 2 ml of an NB medium. The suspension is diluted and spread on an NB agar medium containing 12.5 μg/ml of streptomycin. After incubating at 30° C. for 2 days, colonies formed are replicated on an NB agar medium containing 100 μg/ml of spectinomycin. After incubation at 30° C. for 2 days, colonies formed are picked up as transformants carrying plasmid pCG 4. Thus, *Corynebacterium herculis* ATCC 13868/pCG 4, *Brevibacterium flavum* ATCC 14067/pCG 4 and *Brevibacterium lactofermentum* ATCC 13655/pCG 4 are obtained. The plasmid isolated from these strains in the manner of Example 1 is examined as to cleavage patterns with restriction endonucleases. The plasmid has the same cleavage sites as those of pCG 4.

EXAMPLE 3

In this example, plasmid pCG 11 is constructed by first isolating plasmid pCG 1 from *Corynebacterium glutamicum* 225-57 in the same manner as the isolation of plasmid pCG 4 from *Corynebacterium glutamicum* 225-250. Plasmid pCG 1 is completely digested with Bgl II which is a restriction endonuclease derived from *Bacillus globigii* and is a product of Takara Shuzo Co., and plasmid pCG 4 is completely digested with Bam HI which is a restriction endonuclease produced by Takara Shuzo Co., under suitable conditions for these restriction endonucleases. Then, 0.2 ml of a reaction solution (pH 7.6) consisting of 66 mM Tris-hydrochloride, 6.6 mM $MgCl_2$, 10 mM dithiothreitol, 0.5 mM ATP and 0.5 μg of each of the digested DNA is mixed with 0.1 U of T4 phage DNA ligase (product of Takara Shuzo Co.). The mixture is allowed to react at 4° C. overnight. Protoplasts of *Corynebacterium glutamicum* LA 103 strain are transformed with the ligase reaction solution.

Protoplasts of *Corynebacterium glutamicum* LA 103 are transformed in the same manner as in Example 2 except that the addition of penicillin G during culturing is omitted. Transformation and isolation of transformants are carried out in the same manner as in Example 2. In the transformation procedure, 0.1 ml of the ligase reaction solution mentioned above is used. One of the thus obtained streptomycin resistant strains is treated as in Example 1 except that the addition of penicillin G during culturing is omitted to obtain 50 μg of a plasmid DNA. The plasmid DNA is digested with restriction endonucleases solely or in combination. The DNA fragments formed are analyzed by agarose gel electrophoresis as in Example 1 to determine the molecular weights and cleavage sites for restriction endonculeases. The restriction map of the thus obtained plasmid, namely, pCG 11, with restriction endonucleases, Eco RI, Pst I, Bgl II and Hinc II which is derived from *Haemophilus influenzae* is illustrated in FIG. 1. The broken lines show the ligation sites of Bgl II and Bam HI.

*Corynebacterium glutamicum* LA 103 is transformed with plasmid pCG 11 DNA as described above to obtain a spectinomycin resistant transformant. The transformant has a plasmid having the same cleavage sites for restriction endonucleases as those of pCG 11.

REFERENCE EXAMPLE 1

(1) Isolation of plasmid pCG1 from the cultured cells of *Corynebacterium glutamicum* 225-57:

*Corynebacterium glutamicum* 225-57 (ATCC 31808) is cultured with shaking in an NB medium consisting of 20 g of powdered bouillon, 5 g of yeast extract and 1 l of pure water and adjusted to pH 7.2 at 30° C. for 18 hours. Then, 5 ml of the seed culture is inoculated into 400 ml of a semisynthetic medium consisting of 20 g of glucose, 10 g of $(NH_4)_2SO_4$, 3 g of urea, 1 g of yeast extract, 1 g of $KH_2PO_4$, 0.4 g of $MgCl_2.6H_2O$, 10 mg of $FeSO_4.7H_2O$, 0.2 mg of $MnSO_4.(4-6)H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin, 1 mg of thiamine hydrochloride and 1 l of pure water and the inoculated medium is adjusted to pH 7.2. Culturing is carried out with shaking at 30° C. Optical density (OD) at 660 nm is measured by a Tokyo Koden colorimeter and, at the OD value of 0.2, penicillin G is added to the broth to a final concentration of 0.5 U/ml. Cultivation is continued at 30° C. to an OD value of about 0.6.

Cells are recovered from the culture broth; washed with TES buffer solution (pH 8.0) consisting of (i) 0.03M tris(hydroxymethyl)aminomethane (Tris), (ii) 0.005M EDTA and (iii) 0.05M NaCl and thereafter suspended in a lysozyme solution (pH 8.0) consisting of 25% sucrose, 0.1M NaCl, 0.05M Tris and 0.8 mg/ml lysozyme to make 20 ml of a suspension. The suspension is allowed to react at 37° C. for 4 hours. Then, 2.4 ml of 5M NaCl, 0.6 ml of 0.5M EDTA (pH 8.5) and 4.4 ml of a mixed solution of 4% sodium laurylsulfate and 0.7M NaCl are added successively to the reaction suspension. The mixture is stirred slowly and put on an ice water bath for 15 hours.

Whole lysate is put into a centrifugation tube and centrifuged under 69,400×g at 4° C. for 60 minutes to obtain a supernatant. To the supernatnat is added 10% by weight of polyethyleneglycol 6,000. The mixture is stirred slowly to provide a uniform blend and subjected to an ice water bath. After 16 hours, the mixture is subjected to centrifugation under 1,500×g for 10 minutes to obtain a pellet. The pellet is redissolved in 5 ml of TES buffer solution and 2.0 ml of 1.5 mg/ml ethidium bromide is added. To the mixture is added cesium chloride. After dissolving, the density if adjusted to 1.580. The solution is subjected to centrifugation under 105,000×g at 180° C. for 48 hours.

After the density gradient centrifugation, a circular DNA closed with a covalent bond is found as a high density band located in the lower part of the centrifugation tube by ultraviolet irradiation. The band is taken out from the side of the tube with an injector to obtain a fraction containing plasmid pCG1. The fraction is treated five times with equal amount of isopropylalcohol solution consisting of 90% by volume of isopropylalcohol and 10% TES buffer solution containing saturated amount of cesium chloride to remove ethidium bromide. Then, the residue is subjected to dialysis with TES buffer solution.

To 1 ml of the thus obtained dialysate containing plasmid pCG1 is added 2 ml of ethanol. A precipitate deposits. The deposited precipitate is recovered by centrifugation and dried in vacuo at −20° C. to obtain 50 μg of plasmid pCG1.

(2) Cleavage specificity with various restriction endonucleases and molecular weight of plasmid pCG1:

In this step, 0.5 μg of plasmid pCG1 prepared above is dissolved in 10 μl of TES buffer solution (pH 8.0) and two fold or more restriction endonucleases such as EcoRI, HindIII, BamHI, PstI, Sal I, Hinc II and Kpn I is added under the suitable conditions for each restriction endonuclease. The digested specimen is provided to horizontal 0.8% agalose gel containing 0.6 μg/ml ethidium bromide and electrophoresis is carried out at a constant additional voltage of 7 V per 1 cm in width for 3-4 hours. The number of fragments formed is counted by ultraviolet irradiation on the gel plate. The molecular weight of each fragment is determined from the electrophoretic distance and that of plasmid pCG1 is determined by summing them up. The molecular weight of plasmid pCG1 is determined by reference to a standard curve plotted with electrophoretic distance of each DNA fragment, the molecular weight of which is already known. The DNA fragments are produced by the digestion of λ phage DNA with HindIII and subjected to electrophoresis on the same agalose gel as that for plasmid pCG1. The results are illustrated in the following table.

| Enzyme | Number of cleavage sites | Molecular weight of each fragment (Megadalton) | Molecular weight of pCGl by summing up (Megadalton) |
|---|---|---|---|
| Eco RI | 1 | 2.0 | 2.0 |
| Hind III | 2 | 1.73, 0.27 | 2.0 |
| Hind II | 2 | 1.50, 0.50 | 2.0 |
| Bam HI | 0 | — | — |
| Pst I | 0 | — | — |
| Sal I | 0 | — | — |
| Kpn I | 0 | — | — |

What is claimed is:

1. An isolated plasmid pCG 4 characterized by a molecular weight of about 19 megadaltons, a number of cleavage sites for the restriction endonucleases, Eco RI, Bam HI, Hind III, Pst I and Sal I of 4, 7, 9, 6 and 6 respectively, and carrying a gene for resistance to a least one of streptomycin and spectinomycin.

2. A recombinant plasmid capable of autonomous replication in Corynebacterium or Brevibacterium constructed from the plasmid pCG 4 defined in claim 1 by adding a foreign DNA fragment thereto.

3. A recombinant plasmid capable of autonomous replication in Corynebacterium or Brevibacterium constructed from the plasmid pcG 4 defined in claim 1 by deleting a DNA region that does not affect its function to replicate autonomously or its resistance to at least one of said streptomycin and spectinomycin and adding a foreign DNA fragment to said plasmid.

4. A recombinant plasmid constructed from plasmid pCG 4 defined in claim 1 by deleting a DNA region that does not affect its resistance to at least one of streptomycin and spectinomycin and adding a foreign DNA region conferring a function to replicate autonomously in Corynebacterium or Brevibacterium.

5. A recombinant plasmid according to claim 4 which is plasmid pCG 11 characterized by the restriction map illustrated in FIG. 1 and a molecular weight of 4.5 megadaltons.

6. A recombinant plasmid constructed from plasmid pCG 11 defined in claim 5 by adding a foreign DNA fragment thereto.

7. A biologically pure culture of the microorganism Corynebacterium glutamicum LA 103/pCG 11, ATCC 39022 which carries the plasmid pCG 11.

8. A biologically pure culture of the microorganism Corynebacterium glutamicum 225-250, having the identifying characteristics of ATCC 31830 and which carries the plasmid pCG 4.

9. A biologically pure culture of a microorganism selected from the group consisting of Corynebacterium herculis ATCC 13868/pCG 4, Brevibacterium flavum ATCC 14067/pCG 4 and Brevibacterium lactofermentum ATCC13655/pCG 4 having the identifying characteristics of ATCC 31837, 31838 and 31839 respectively and carrying the plasmid pCG 4.

* * * * *

UNITED STATES PATENT AND TRADEMARK OFFICE
CERTIFICATE OF CORRECTION

PATENT NO. : 4,500,640

DATED : February 19, 1985

INVENTOR(S) : RYOICHI KATSUMATA, et al.

It is certified that error appears in the above-identified patent and that said Letters Patent is hereby corrected as shown below:

Cover Page, insert as follows:

--[30] Foreign Application Priority Data

April 17, 1981 [JP] Japan 56/58186--

Column 11, line 23, "Hind II" should read --Hinc II--

Signed and Sealed this

Thirteenth Day of August 1985

[SEAL]

Attest:

DONALD J. QUIGG

Attesting Officer    Acting Commissioner of Patents and Trademarks